(12) United States Patent
Chang et al.

(10) Patent No.: US 6,894,039 B2
(45) Date of Patent: May 17, 2005

(54) SELENOPHENE ANTI-TUMOR AGENTS

(75) Inventors: Ching-jer Chang, West Lafayette, IN (US); Curtis L. Ashendel, West Lafayette, IN (US); Darrick Kim, Chicago, IL (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 10/658,175

(22) Filed: Sep. 9, 2003

(65) Prior Publication Data
US 2004/0063662 A1 Apr. 1, 2004

Related U.S. Application Data

(62) Division of application No. 10/061,480, filed on Feb. 1, 2002, now Pat. No. 6,620,804, which is a continuation of application No. 09/180,514, filed as application No. PCT/US97/09717 on Nov. 11, 1998, now abandoned.
(60) Provisional application No. 60/019,095, filed on Jun. 3, 1996.

(51) Int. Cl.$^7$ .................. C07D 421/04; A61P 35/00; A61K 31/33; A61K 31/381; A61K 31/341
(52) U.S. Cl. .................. 514/183; 540/1; 548/517; 549/59; 549/429; 514/461; 514/444
(58) Field of Search ............... 540/1; 514/183, 514/461, 444; 548/517; 549/59, 429

(56) References Cited

U.S. PATENT DOCUMENTS 5,578,636 A    11/1996   Chang et al. ............... 514/444

OTHER PUBLICATIONS

Allessandro, et al. Ric. Sci, Rend., Sez. A (1965), 8(6), 1537–9.*
Chem. Abstr., vol. 113, No. 21, Nov. 19, 1990 (Columbus, OH, USA), p. 695, column 2, the abstract No. 191079S, Shabana et al. "Synthesis of Mixed Oligomeric Heteroarylenes Containing Unsubstituted Furan, Thiopene, and Selemophene Rings; Their UV Spectra and Oxidation Potentials." Phosphorus, Sulfur, Silicon Related Elem. 1990, 48(1–4), 239–44 (Eng.), see entire Abstract.
Chem. Abstr., vol. 112, No. 5, Jan. 29, 1990 (Columbus, OH, USA), p. 554, column 12, the abstract No. 35596g, Zimmer, H. et al. "Synthesis of Mixed Oligomeric Heteroarylenes Containing Furan, Thiopene, and Selenophene Rings; Their UV Spectra and Oxidation Potentials," Phosphorus, Sulfur, Silicon Related Elem. 1989, 42(3–4), 171–6 (Eng.) see entire Abstract.
Chem. Abstr., vol. 110, No. 15, Apr. 10, 1989 (Columbus, OH, USA), p. 650, columns 1–2, the abstract No. 134566n, Shabana, R. et al. "Synthesis of Mixed Heteroarylenes Containing Thiopene and Selenophene Rings. Their UV Spectra and Oxidation Potentials." J. Chem. Soc. Chem. Commun. 1988, (15), 988–9 (Eng.), see entire Abstract.
Photochemistry and Photobiology, vol. 39, No. 4, pp. 521–524, 1984 (Great Britain), "Research Note: Comparison of The Phototoxicity of α–Terthienyl With That of a Selenium and of an Oxygen Analogue.".
Allesandro, et al. Ric. Sci., Rend., Sez. A (1965), 8(6), 1537–9.
Mikhaleva, et al., Synthesis of 2–(2–Selenienyl)Pyrrole from Methyl–2–Selenienylketoxime and Acetylene, Chem. Heterocycl. Comp., vol. 28, No.5, pp. 599–601 (1992).
Fringuell, et al., Heteroaromatic Rings as Substituents, J. Chem Soc. Perkin Transactions, vol. 2, pp. 971–975 (1980).
Novak, et al., Electronic Structure of Bichalcophenes, J. Phys. Chem., vol. 98, No. 20, pp. 5240–5243 (1994).
Yui, et al., Extensively Conjugated Homologues of Selenophene—TCNQ as New Electron Acceptors, Chem. Letters, pp. 1179–1182 (1988).

* cited by examiner

Primary Examiner—Mark L. Berch
Assistant Examiner—Kahsay Habte
(74) Attorney, Agent, or Firm—Barnes & Thornburg LLP

(57) ABSTRACT

Novel selenophene compounds useful as anti-tumor agents are described. Preferred compounds include compounds of formula I:

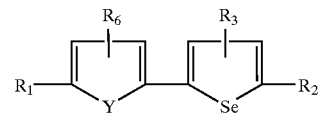

wherein $R_1$ and $R_2$ are independently selected from the group consisting of;

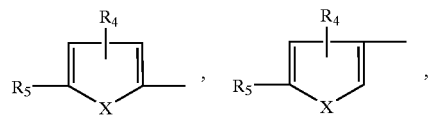

H, CHO, $CH_2OH$ and $CH_2NH_2$; and

X and Y are independently selected from the group consisting of Se, S, O, $NCH_3$ and NH. Pharmaceutical compositions and a method for treating patients having tumors utilizing the disclosed selenophene compounds are also described.

8 Claims, No Drawings

SELENOPHENE ANTI-TUMOR AGENTS

CROSS REFERENCE TO RELATED APPLICATIONS

This application is a divisional application of U.S. patent application Ser. No. 10/061,480, filed on Feb. 1, 2002, now U.S. Pat. No. 6,620,804 which a continuation application of U.S. patent application Ser. No. 09/180,514, filed on Nov. 11, 1998, now abandoned which is a U.S. national application of international application serial No. PCT/US97/09717, filed on Jun. 3, 1997, which claims priority to U.S. provisional application Ser. No. 60/019,095, filed on Jun. 3, 1996.

GOVERNMENT RIGHTS

This invention was made with United States Government support under Grant No. UO1 CA50743, awarded by the National Cancer Institute. The United States Government has certain rights in the invention.

FIELD OF THE INVENTION

The present invention relates to compositions and a method for treating a patient having a tumor. More specifically, the present invention relates to the treatment of such patients with an effective amount of a selenophene derivative.

BACKGROUND AND SUMMARY OF THE INVENTION

The control and cure of cancer represents one of our most challenging health problems. The treatment of cancer can be approached by several modes of therapy including surgery, radiation, chemotherapy or a combination of any of these treatments. Chemotherapy continues to be an indispensable therapy for inoperable or metastatic forms of the disease.

The selection of natural compounds, or the synthesis of new compounds having effective anticancer activity is complicated by the still limited knowledge of cancer cell biology and biochemistry. Therefore, development of new effective anti-tumor agents will remain heavily dependent on screening compounds to discover novel compounds having cytotoxic activity. Preferably, such compounds exhibit enhanced cytotoxicity against tumor cells relative to their cytotoxicity to normal cells.

The success of novel antitumor drug development programs is dependent on the initial identification of antitumor agents. Thus the discovery of antitumor agents requires the systematic screening of a large number of natural products and synthetic compounds.

The mouse L1210 leukemia cell line was initially the preferred model system used for screening natural compounds for antitumor activity. However, the P388 murine leukemia system was found to be more sensitive and predictive than L1210 leukemia system, and has been used as primary screen during the past decade. Systematic screening for compounds exhibiting toxicity to these two leukemia cell lines has resulted in the isolation of a large number of active natural products. However, the anticancer activities of these compounds were predominantly in leukemia, lymphoma and a few rare tumors. Low clinical efficacy, or the lack of clinical efficacy of known chemotherapeutics against slower growing solid tumors, is a serious concern.

It has been recognized that the use of a single antileukemia screening system could bias the end results and lead to the isolation of compounds only active in the treatment of fast growing tumors. In addition, the use of a single anti-leukemia screening system may not detect novel compounds with high specificities for particular cell lines. It is also likely that many novel compounds with possible anti-tumor activity have remained undetected by the less sensitive in vivo models due to the low concentrations at which many active natural products occur.

Considering the diversity of tumors in terms of cell type, morphology, growth rate and other cellular characteristics, the U.S. National Cancer Institute (NCI) has developed a "disease-oriented" approach to antitumor activity screening (M. R. Boyd, in "Principle of Practice of Oncology" J. T. Devita, S. Hellman, S. A. Rosenberg (Eds.) Vol. 3, PPO Update, No. 10, 1989). This in vitro prescreening system is based on the measurement of antitumor cytotoxicity against human tumor cell line panels consisting of approximately 60 cell lines of major human tumors (including leukemia and slower growing tumor cells such as lung, colon, breast, skin, kidney, etc.). The most important advantage of the new in vitro screening panels is the opportunity to identify compounds that are selectively more cytotoxic to cells of slowly growing solid tumors than to rapidly growing leukemia cells.

The cytotoxicity profile of the NCI human tumor cell panels displays the tumor specificity of a given compound, however the assay does not assess the toxicity of that compound to normal human cells. Accordingly a second bioassay is utilized to measure the selective cytotoxicity against certain types of tumor cells verses normal human cells.

The growth and differentiation of cells are regulated by signaling cascades induced by various mitogenic proteins (J. Kurjan and B. L. Taylor, "Signal Transduction," Academic Press, New York, N.Y. 1994) that often are encoded by proto-oncogenes. The overexpression, amplification or mutation of the oncoprotein is critically involved in the initiation, progression and metastasis of malignant cells (R. A. Weinberg, "Oncogenes and the Molecular Origins of Cancer," Cold Spring Harbor Laboratory Press, Cold Spring Harbor, N.Y., 1989). Many oncoproteins alter normal cellular growth regulation by modulating the intracellular signaling pathways from the membrane to the nucleus. Therefore, cancer may be considered as a disease of cellular signal transduction, which presents a novel approach for anticancer therapy. One of the critical enzymes involved in the oncoprotein signal transduction is protein kinase C (U. Nishizuka, *Nature*, 308, 693, 1984 and *Science*, 233, 305, 1986). Thus, the determination of a compound's ability to inhibit protein kinase C activity has become a good prognostic for discovering novel anticancer agents (A. Basu, *Pharmac Ther*, 59, 257, 1993). Furthermore it is anticipated that the selenophene compounds will demonstrate selectivity for certain class members of protein kinases, including protein kinase C. Inhibition of a specific classes of protein kinases will allow the treatment of other diseases associated with defects in signaling transduction.

Selenophenes are selenium containing heterocyclic compounds that are analogs of naturally occurring thiophene, furan and pyrrole compounds. Selenophenes have been found to be effective antitumor agents, and exhibit enhanced cytotoxicity against slow growing tumor cells, selective cytotoxicity against human renal, ovarian tumor cells, and skin tumor cells; and exhibit inhibition of protein kinase C.

In accordance with this invention there is provided a method for the treatment of cancer which utilizes selenophene compounds of the formula I:

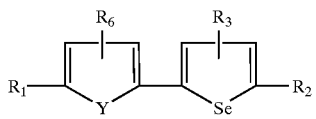

wherein $R_1$ and $R_2$ are independently selected from the group consisting of,

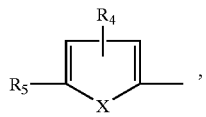

H, CHO, $CH_2OH$ and $CH_2NH_2$;

X and Y are independently selected from the group consisting of Se, S, O, $NCH_3$ and NH;

$R_3$, $R_4$, $R_5$ and $R_6$ are independently selected from the group consisting of H, CHO, $CH_2OH$ and $CH_2NH_2$; cyclodextrin complexes of such compounds; and when $R_3$, $R_4$, $R_5$ or $R_6$ is $CH_2NH_2$, the pharmaceutically acceptable salt of the compound represented thereby.

Further in accordance with this invention there are provided novel cytotoxic compounds of the above formula and chemotherapeutic pharmaceutical compositions containing said compounds in anti-tumor effective amounts.

Additional objects, features, and advantages of the invention will become apparent to those skilled in the art upon consideration of the following detailed description of preferred embodiments exemplifying the best mode of the invention as presently perceived.

DETAILED DESCRIPTION OF THE INVENTION

The present invention is directed to selenophene compounds, their pharmaceutical compositions and methods utilizing such compounds/compositions for treating patients, having tumor. The selenophene compounds are effective antitumor agents against slow growing tumors, and generally have been found to exhibit high selective cytotoxicity for individual tumor cell lines.

The present selenophene compounds are readily prepared usin art-recognized chemical synthesis procedures as exemplified in Example 1 and in Examples 3–8. This invention is further envisioned from the chemical concept on the basis of a coherent design as shown in Scheme 3 in Example 2. This chemical concept provides the foundation for conceiving the preparation and utility of numerous "hybrid" selenophene compounds containing other related five-membered heterocycles, such as furan, thiophene and pyrrole, and their analogs. Moreover, the practice of this chemical concept is substantiated by Example 2 and by Examples 9–33. The anticancer utility of these hybrid selenophene compounds is manifested by (a) selective cytotoxicity for human renal carcinoma cells in comparison to normal human renal cells (Table 1), (b) antitumor cytotoxicity against a variety of human tumor cells (Example 53), (c) in vivo antitumor activity against human lung tumor (Example 54), and (d) inhibition of protein kinase C activity (Table 2).

In corroboration with the above chemical concept, a versatile, alternative synthetic design is further conceived for the preparation of relevant "hybrid" selenophene compounds as in the scheme shown in Example 34. The practice of this synthetic design is supported by Examples 34–50.

The anticancer utility of these hydrid selenophene compounds is indicated by (a) selective cytotoxicity for human renal carcinoma cells in comparison to normal human renal cells (Table 1), (b) antitumor cytotoxicity against a variety of human tumor cells (Example 53), (c) in vivo antitumor activity against human lung tumor (Example 54) and (d) inhibition of protein kinase C (Table 2).

The compounds of the present invention are selenophene compounds of the formula I:

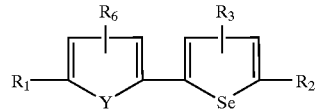

wherein $R_1$ and $R_2$ are independently selected from the group consisting of;

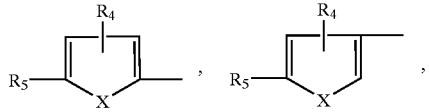

H, CHO, $CH_2OH$ and $CH_2NH_2$;

X and Y are independently selected from the group consisting of Se, S, O and NR;

R is H or $C_1$–$C_7$ alkyl;

$R_3$, $R_4$, $R_5$ and $R_6$ are independently selected from the group consisting of nitro, amino, alkoxy, cyano, chloro, bromo, iodo, $C_1$–$C_7$ alkyl or haloalkyl, $C_1$–$C_7$ alkenyl or haloalkenyl, $C_1$–$C_4$ alkanoyloxy methyl, $CH_2OR_7$, $COR_8$, $CH_2NR_9R_{10}$, $CH(OR_7)R_{11}$, $CH=CR_{12}R_{13}$, $CH=NR_{14}$, $CH_2SC(NH)NH_2$ and $C\equiv CR_{15}$ wherein $R_7$ is H, $CO(CH_2)_2CO_2H$, $(CH_2)_2OCH_3$, $C_1$–$C_4$ alkyl or $COC_1$–$C_1$, alkyl;

$R_8$ is H or $C_1$–$C_7$ alkyl;

$R_9$ and $R_{10}$ are independently H, CN, $C_1$–$C_4$ alkyl, or mono- or di-hydroxy$C_2$–$C_4$ alkyl;

$R_{11}$ is $C_1$–$C_7$ alkyl, or $C_1$–$C_7$ alkenyl;

$R_{12}$ and $R_{13}$ are independently H, $C_1$–$C_7$ alkyl, $COOR_8$, CN, $CH(OR_7)COOR_8$, Br, CO-thienyl, $COC_6H_4OH(p)$;

$R_{14}$ is $NHR_7$ or $OR_8$;

$R_{14}$ is $COOR_8$, $CH(OR_7)CH_2OR_{16}$ or $CH(OCOC_1$–$C_4$ alkyl)$CH_2OR_8$;

$R_{16}$ is H, $COCH_2CH_2CO_2H$, or $COC_1$–$C_7$ alkyl;

cyclodextrin complexes of such compound and when $R_3$, $R_4$, $R_5$ or $R_6$ is $CH_2NR_6R_7$, the pharmaceutically acceptable salt of the compound represented thereby.

In one preferred embodiment of this invention there is provided anti-tumor selenophenes of the above formula I, wherein $R_2$ is

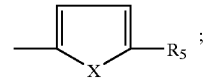

X and Y are independently selected from the group consisting of S, Se and NH;

$R_1$ $R_3$, and $R_6$ are H; and $R_5$ is selected from the group consisting of CHO or $CH_2OH$; and cyclodextrin complexes of such compounds. These compounds have been demonstrated to exhibit cytotoxic selectivity against transformed human cells (See Table 1).

In another preferred embodiment of this invention there is provided anti-tumor selenophenes of the above formula I wherein $R_1$ is

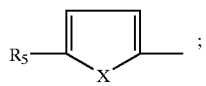

X and Y are independently selected from the group consisting of S, Se and NH;

$R_2$, $R_3$, and $R_6$ are H;

$R_5$ is selected from the group consisting of CHO or $CH_2OH$; and cyclodextrin complexes of such compounds.

Other preferred compounds in accordance with this invention are selenophenes of formula I:

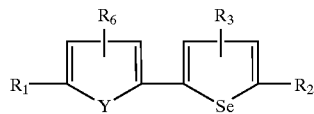

wherein $R_1$ and $R_2$ are independently selected from the group consisting of;

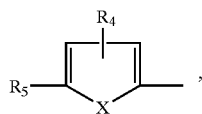

H, CHO, $CH_2OH$ and $CH_2NH_2$;

X and Y are independently selected from the group consisting of Se, S, O, $NCH_3$, and NH;

$R_3$, $R_4$, $R_5$ and $R_6$ are independently selected from the group consisting of H, CHO, $CH_2OH$ and $CH_2NH_2$; cyclodextrin complexes of such compounds; and when $R_2$ or $R_3$ is $CH_2NH_2$, the pharmaceutically acceptable salt of the compound represented thereby; with the proviso, that when $R_2$ is

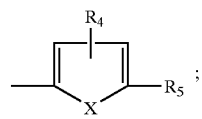

$R_1$ is other than

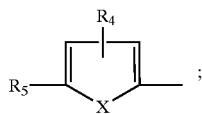

and when $R_1$ is

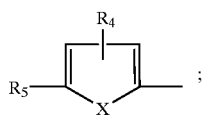

$R_2$ is other than

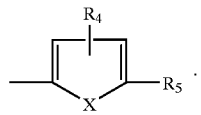

In accordance with another embodiment of the present invention novel intermediates of Formula II are also provided:

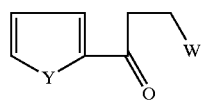

wherein W is selected from the group consisting of $N(CH_3)_2$ and

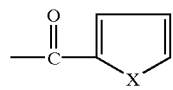

and X and Y are independently selected from the group consisting of Se, S, O, $NCH_3$ and NH.

One aspect of the present invention is a method of preparing the compounds of Formula I through an intermediate a compound of the formula:

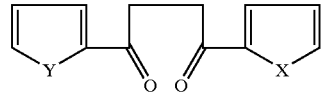

in accordance with the general methods of schemes 1–4 as described hereinbelow, wherein X and Y are independently selected from the group consisting of Se, S, O, $NCH_3$ and NH.

The selenophene compounds of this invention are readily formulated into pharmaceutical compositions, also within the scope of this invention, for use in the presently described method for treatment of patients having tumors. In one preferred embodiment of this invention, the pharmaceutical composition comprises an anti-tumor effective amount of a selenophene compound of formula I:

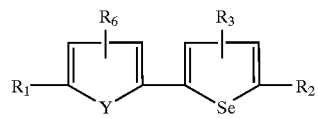

wherein $R_1$ and $R_2$ are independently selected from the group consisting of;

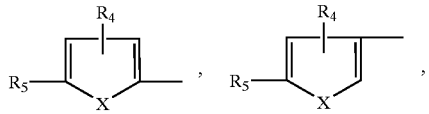

H, CHO, $CH_2OH$ and $CH_2NH_2$;

X and Y are independently selected from the group consisting of Se, S, O and NR, wherein R is H or $C_1$–$C_7$ alkyl;

$R_3$, $R_4$, $R_5$ and $R_6$ are independently selected from the group consisting of nitro, amino, alkoxy, cyano, chloro, bromo, iodo, $C_1$–$C_7$ alkyl or haloalkyl, $C_1$–$C_7$ alkenyl or haloalkenyl, $C_1$–$C_4$ alkanoyloxy methyl, $CH_2OR_7$, $COR_8$, $CH_2NR_9R_{10}$, $CH(OR_7)R_{11}$, $CH=CR_{12}R_{13}$, $CH=NR_{14}$, $CH_2SC(NH)NH_2$ and $C\equiv CR_{15}$ wherein $R_7$ is H, $CO(CH_2)_2CO_2H$, $(CH_2)_2OCH_3$, $C_1$–$C_4$ alkyl or $COC_1$–$C_{17}$ alkyl;

$R_8$ is H or $C_1$–$C_7$ alkyl;

$R_9$ and $R_{10}$ are independently H, CN, $C_1$–$C_4$ alkyl, or mono- or di-hydroxy$C_2$–$C_4$ alkyl;

$R_{11}$ is $C_1$–$C_7$ alkyl, or $C_1$–$C_7$ alkenyl;

$R_{12}$ and $R_{13}$ are independently H, $C_1$–$C_7$ alkyl, $COOR_8$, CN, $CH(OR_7)COOR_8$, Br, CO-thienyl, $COC_6H_4OH(p)$;

$R_{14}$ is $NHR_7$ or $OR_8$;

$R_{15}$ is $COOR_8$, $CH(OR_7)CH_2OR_{16}$ or $CH(OCOC_1$–$C_4$ alkyl$)CH_2OR_8$;

$R_{16}$ is H, $COCH_2CH_2CO_2H$, or $COC_1$–$C_7$ alkyl;

cyclodextrin complexes of such compound and when $R_3$, $R_4$, $R_5$ or $R_6$ is $CH_2NR_6R_7$, the pharmaceutically acceptable salt of the compound represented thereby, and a pharmaceutically acceptable carrier.

Another pharmaceutical composition within the scope of this invention comprises an anti-tumor effective amount of a selenophene compound of the formula I:

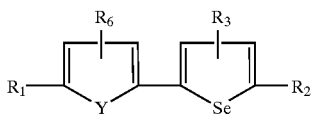

I wherein $R_1$ and $R_2$ are independently selected from the group consisting of;

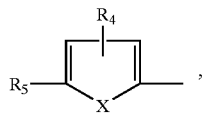

H, CHO, $CH_2OH$ and $CH_2NH_2$;

X and Y are independently selected from the group consisting of Se, S, O, $NCH_3$ and NH;

$R_3$, $R_4$ and $R_6$ are H;

$R_5$ is selected from the group consisting of H, CHO, $CH_2OH$ and $CH_2NH_2$; cyclodextrin complexes of such compounds; and when $R_3$, $R_4$, $R_5$ or $R_6$ is $CH_2NH_2$, the pharmaceutically acceptable salt of the compound represented thereby; with the proviso, that when $R_2$ is

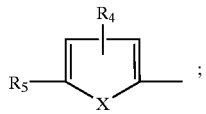

$R_1$ is other than

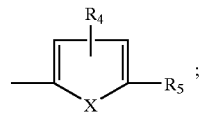

and when $R_1$ is

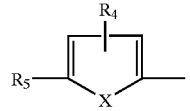

$R_2$ is other than

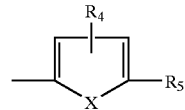

and a pharmaceutically acceptable carrier.

The present compounds are readily prepared using art-recognized chemical-synthesis procedures as exemplified hereinbelow.

The cytotoxic activity of the present selenophene compounds have been measured utilizing two different assays or screens. The first screen measures the cytotoxicity against a, panel of sixty different human tumor cell lines. This assay provides data regarding the general cytotoxicity of an individual compound. In particular this type of assay is useful in identifying compounds which have enhanced cytotoxic activity against slow growing tumors as compared to faster growing tumor cells such as leukemia tumor cell lines. The identification of such compounds is critical since previously identified antitumor agents have low cytotoxic activity against slower growing tumors. The specificity of a compound for a limited number of tumor cell lines also indicates that such a compound will likely be less cytotoxic to normal cells. The specificity of a cytotoxic compound for tumor cell lines relative to normal cells is an important characteristic of an effective antitumor agent.

Antitumor cytotoxicity data generated from the National Cancer Institute human tumor cell panels can also be expressed in a graphic pattern (mean graph) to display differential cell growth inhibition (K. D. Paull, R. H. Shoemaker, L. Hodes, A. Monks, D. A. Scudiero, L. Rubinstein, J. Plowman and M. R. Boyd, *J. Natl. Cancer Inst.*, 81, 1088, 1989.) In the mean graph, the arithmetic mean of the logarithm of the $GI_{50}$ (50% growth inhibition), TGI (total growth inhibition) or $LC_{50}$ (50% lethal concentration) values is used as an anchor point. Relative cytotoxicity is displayed by projecting bars to the right or left of the mean, depending on whether cell sensitivity to a test compound is more or less than average. The length of a bar is indicative of differential cytotoxicity against a specific type of tumor cells or tumor panels.

In a second assay, the cytotoxic selectivity is assessed by comparing compound cytotoxicity against human renal carcinoma cells (A-498), ras-transformed human bronchial epithelial cells (TBE) and normal human renal cells (RPTEC). $IC_{50}$ values were compared between treated TBE cells and RPTEC cells and the selective cytotoxicity index (SCI) was determined [SCI=$GI_{50}$(RPTEC)/$GI_{50}$(A-498)].

The antitumor cytotoxicity of the selenophene compounds tested in those in vitro assays was measured by a microculture assay using either a 3-(4,5-dimethylthiazol-2-yl)-2,5-diphenyltetrazolium bromide (MTT) or sulforhodamine B (SRB) based assay. [M. R. Boyd in "Principles and Practices of Oncology," V. T. DeVita, Jr.]. The experiments were conducted at Purdue University in 96-well microtiter plates and the cytotoxic effects of the selenophene compounds on those cells were measured by cell count using a Coulter Z. F. counter (Hialeah, Fla.). The results are expressed as $GI_{50}$, the concentration of drug at which cell numbers are reduced to 50% of control cell culture [T. C. K. Chan, C. J. Chang, N. M. Koonchanok and R. L. Geahlen, *Biochem. Biophys. Res. Commun.*, 193, 1152, (1993); S. Hellman and S. A. Rosenberg (Eds.), Vol. 3, PPO Updates, Number 10, (1989).]

This in vitro microculture assay has an advantage over in vivo assays in that results are obtained within a week as opposed to several months. The MTT assay is based on the production of a dark blue formazan product by dehydrogenase in the mitochondria of live tumor cells after exposure to drug for 6 days [M. C. Alley, D. A. Scudiero, A. Monks, M. L. Hursey, M. J. Czerwinski, D. L. Fine, B. J. Abbott, J. G. Mayo, R. H. Shoemaker and M. R. Boyd, *Cancer Res.*, 48, 589, 1988]. Thus, only live cells are stained and can be measured at 570 nm. The SRB assay is based on the binding of the anionic group to the basic amino acid residues of cellular proteins after exposure of tumor cells to drug for 2 days [P. Skehan, R. Storeng, D. Scudiero, A. Monks, J. McMahon, D. Vistica, J. T. Warren, H. Bohesch, S. Kenney and M. R. Boyd, *J. Nat. Cancer Inst.*, 82, 1107, 1990.] Thus, the total protein can be measured at 564 nm. Antitumor cytotoxicity is reported as $GI_{50}$, effect drug dose at which cell growth is retarded to 50% of control culture of tumor cells. The active compounds are defined as those compounds having $GI_{50}$ values that are less, than $10^{-4}$ M or 10 μg/ml.

The data presented in Table 1 illustrates that selenophenes generally exhibit greater cytotoxicity for human renal carcinoma cells in comparison to the normal human cells. The data of Table 1 demonstrates the selective cytotoxicity of various selenophene compounds against human renal carcinoma and ras-oncogene transformed human bronchial epithelial cells [in $GI_{50}$(ug/ml)]. The following abbreviations are used for the tested cell lines:

TABLE 1

| NSC Number | $GI_{50}$ (μg/ml) | | | |
|---|---|---|---|---|
| | RPTEC | A-498 | TBE | SCI |
| 674973 | $4 \times 10^0$ | $3 \times 10^0$ | $4 \times 10^0$ | 1 |
| 675246 | $1 \times 10^{-1}$ | $3 \times 10^{-6}$ | $3 \times 10^{-3}$ | >1000 |
| | $3 \times 10^{-2}$ | $3 \times 10^{-6}$ | $2 \times 10^{-3}$ | >1000 |
| 675247 | $2 \times 10^{-1}$ | $7 \times 10^{-5}$ | $3 \times 10^1$ | >1000 |
| | $8 \times 10^0$ | $2 \times 10^{-6}$ | $2 \times 10^1$ | >1000 |
| 676628 | $4 \times 10^2$ | $8 \times 10^1$ | $1 \times 10^2$ | 5 |
| 676632 | $2 \times 10^{-3}$ | $3 \times 10^{-7}$ | $<10^{-3}$ | >1000 |
| | $3 \times 10^{-4}$ | $2 \times 10^{-7}$ | $2 \times 10^{-4}$ | >1000 |
| 675347 | $2 \times 10^1$ | $3 \times 10^1$ | $1 \times 10^1$ | <1 |
| 675344 | $<10^{-2}$ | $3 \times 10^{-7}$ | $<10^{-2}$ | >1000 |
| | $1 \times 10^{-4}$ | $6 \times 10^{-8}$ | $7 \times 10^{-6}$ | >1000 |
| 676633 | $2 \times 10^1$ | $1 \times 10^2$ | $1 \times 10^1$ | <1 |
| 676634 | $1 \times 10^1$ | $6 \times 10^{-4}$ | $3 \times 10^{-4}$ | >1000 |
| | $4 \times 10^{-1}$ | $3 \times 10^{-3}$ | $6 \times 10^{-3}$ | >100 |
| 676635 | $2 \times 10^0$ | $<10^{-3}$ | $2 \times 10^1$ | >1000 |
| 123127 | $5 \times 10^{-2}$ | $5 \times 10^{-2}$ | $3 \times 10^{-2}$ | 1 |

| NSC Number | Structure |
|---|---|
| 674973 | 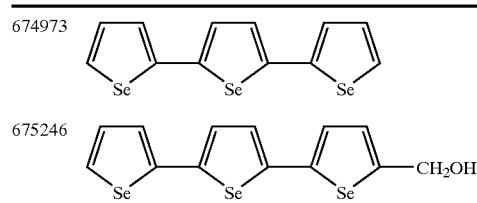 |
| 675246 | |
| 675247 | 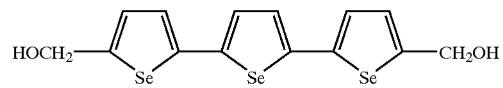 |
| 676628 | 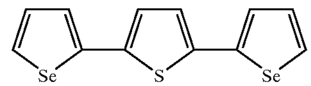 |
| 676632 | 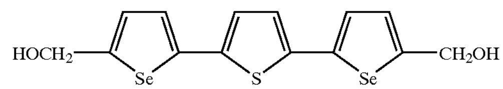 |
| 675347 | 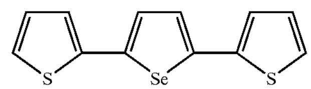 |
| 675344 | 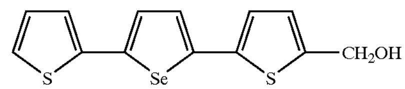 |
| 676633 | 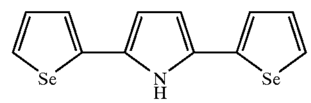 |
| 676634 | 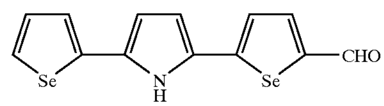 |
| 676635 | 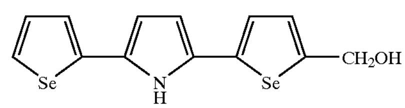 |
| 123127 | Adriamycin |

RPTEC: normal human renal cells
A-498: human renal carcinoma
TBE: ras-transformed human bronchial epithelial cells
SCI: selectively cytotoxicity index = $GI_{50}$ (RPTEC)/$GI_{50}$ (A-498)

The present invention further provides pharmaceutical formulations comprising an effective amount of a selenophene compound for treating a patient having a tumor. As used herein, an effective amount of the selenophene compound is defined as the amount of the compound which, upon administration to a patient, inhibits growth of tumor cells, kills malignant cells, reduces the volume or size of the tumors or eliminates the tumor entirely in the treated patient.

The effective amount to be administered to a patient is typically based on body surface area, patient weight, and patient condition. The interrelationship of dosages for animals and humans (based on milligrams per meter squared of body surface) is described by Freireich, E. J., et al., *Cancer Chemother Rep.*, 50 (4): 219 (1966). Body surface area may be approximately determined from patient height and weight (see e.g., Scientific Tables, Geigy Pharmaceuticals, Ardley, N.Y., pages 537–538 (1970)). An effective amount of the selenophene compounds in the present invention can range from about 5 mg/kg to about 100 mg/kg, more preferably from about 0.25 mg/kg to about 50 mg/kg, and most preferably about 0.1 to about 10 mg/kg.

Effective doses will also vary, as recognized by those skilled in the art, dependant on route of administration, excipient usage and the possibility of co-usage with other therapeutic treatments including other anti-tumor agents, and radiation therapy.

The pharmaceutical formulation may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable liquid carrier. In one preferred aspect of the present embodiment, the selenophene compound is dissolved in a saline solution containing 5% of dimethyl sulfoxide and 10% Cremphor EL (Sigma Chemical Company). Additional solubilizing agents such as cyclodextrins, which form specific, more soluble complexes with the present selenophene compounds, or other solubilizing agents well-known to those familiar with the art, can be utilized as pharmaceutical excipients for delivery of the selenophene compounds.

The present compound can also be formulated into dosage forms for other routes of administration utilizing well-known methods. The pharmaceutical compositions can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with conventional procedure by compressing mixtures of the active polythiophene and solid carriers, and lubricants well-known to those familiar with the art. Examples of solid carriers include starch, sugar, bentonite. The compounds of the present invention can also be administered in a form of a hard shell tablet or capsule containing, for example, lactose or mannitol as a binder and conventional fillers and tableting agents.

The following examples are provided to illustrate various embodiments of Applicants' invention, and are not intended to in any way limit the scope of the invention as set forth in this specification and appended claims.

EXAMPLE 1
Synthesis of α-Terselenophenes

A two-step total synthesis of α-terselenophene from selenophene (Aldrich Chemical Co.) has been developed (See Scheme 1).

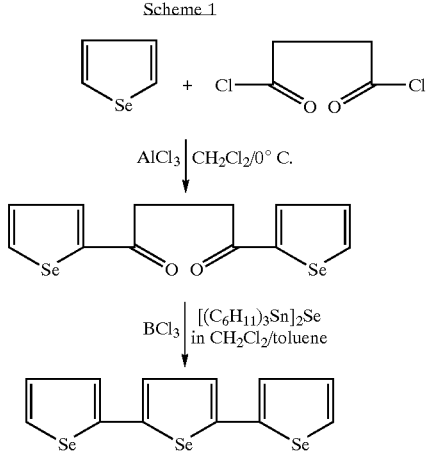

Bis(tricyclohexyltin)selenide can be prepared from tricyclohexyltin chloride (Aldrich Chemical Co.) and sodium selenide (Alfa Chemical Co.). The functional group can be introduced through selective α-formylation using lithium diisopropylamide (LDA) and dimethylformamide (DMF), which can then be sequentially converted into hydroxylmethyl and aminomethyl functional groups. These functional groups can provide required starting points for further chemical modifications, see Scheme 2 as follows:

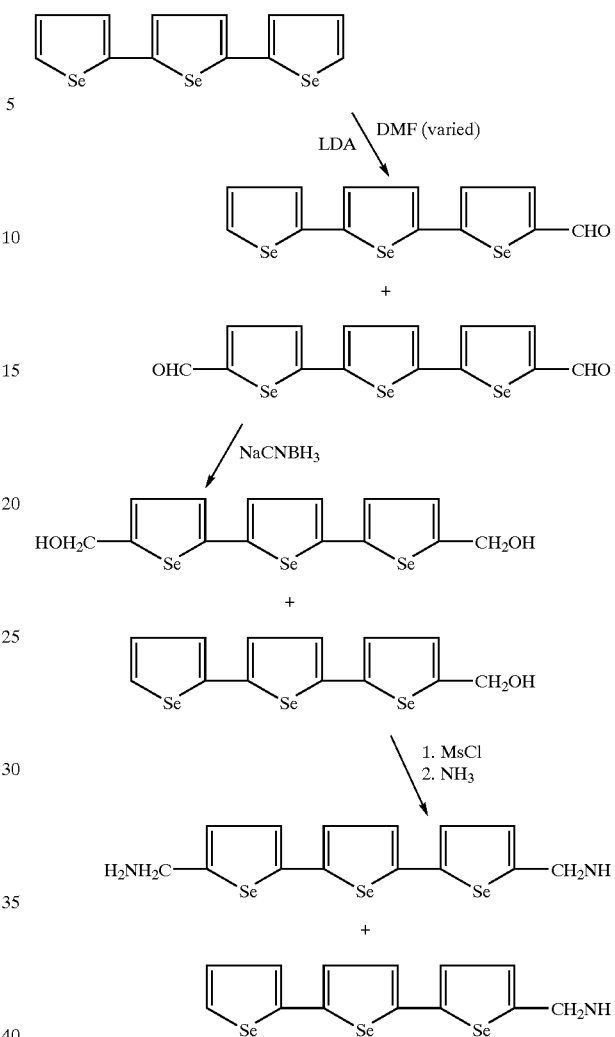

EXAMPLE 2
Synthesis of Hybrid α-Terselenophenes

The synthetic strategy designed for the preparation of α-terselenophene can be readily modified for the synthesis of numerous "hybrid" α-selenophenes containing other five-membered heterocycles (See Scheme 3).

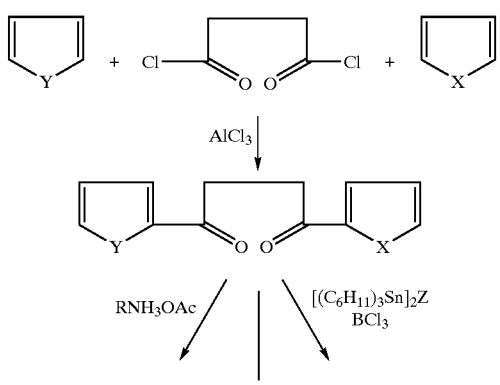

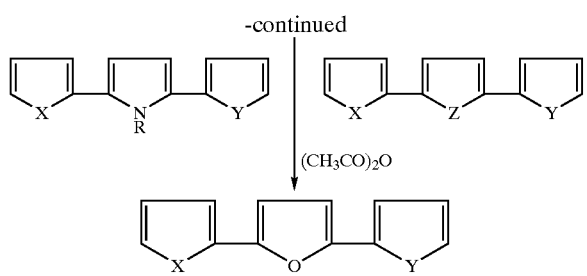

Wherein X, and Y are selected from the group consisting of Se, O, S, NCH$_3$ and NH$_2$, and Z is selected from the group consisting of Se, S, NCH$_3$ and NH$_2$. Various functional groups can be introduced using the approaches outlined in the synthesis of α-terselenophenes (Scheme 2).

EXAMPLE 3
Preparation of 1,4-diselenophene-1,4-diketone.

A CH$_2$Cl$_2$ solution containing selenophene (5 g) and succinyl chloride (2 g) was added dropwise to an anhydrous CH$_2$Cl$_2$ solution (60 mL) containing AlCl$_3$ (5 g) under N$_2$ at 0° C. The reaction mixture was stirred at 0° C. for 1 h, slowly warmed to room temperature, and stirred for 4 h at room temperature. The reaction mixture was poured into a beaker containing ice. Ethyl acetate (200 mL) was added and the organic layer was separated out using a separatory funnel. The aqueous layer was back washed with ethyl acetate (2×100 mL). The combined organic layer was washed with H$_2$O (2×300 mL). The organic layer was collected, dried over MgSO$_4$, and the solvent was removed under vacuum. The residue was chromatographed over silica gel using (10:1) hexanes/ethyl acetate to afford the product in 25% yield.

EXAMPLE 4
Preparation of 2,2':5',2"-terselenophene.

A BCl$_3$ solution (1;0 M solution in hexanes, 580 mL) was added dropwise to an anhydrous toluene solution (5 mL) containing 1,4-diselenophene-1,4-diketone (100 mg) and bis(tricyclohexyltin)selenide (520 mg) under N$_2$ at room temperature. The solution was refluxed for 30 min and cooled to room temperature. The reaction solution was diluted with ethyl acetate (100 mL) and washed with H$_2$O (2×100 mL). The organic layer was separated, dried over MgSO$_4$, filtered, and the solvent was removed under vacuum. The residue was chromatographed over silica gel using hexanes to afford 2,2':5'2"-terselenophene in 80% yield.

EXAMPLE 5
Preparation of 2-formyl-5,2':5",2"-terselenophene.

LDA (1.0 M solution in THF, 310 mL) was added to an anhydrous THF solution (4 mL) containing 2,2':5',2"-terselenophene (100 mg) under N$_2$ at −78° C. The solution was stirred at −78° C. for 3 h, anhydrous DMF (1 mL) was added, stirred at −78° C. for 1 h, and slowly warmed to room temperature. The reaction solution was diluted with ethyl acetate (100 mL) and washed with H$_2$O (4×100 mL). The organic layer was separated, dried over MgSO$_4$, filtered, and the solvent was removed under vacuum. The residue was chromatographed over silica gel using CH$_2$Cl$_2$ to afford 2-formyl-5,2':5',2"-terselenophene in 75% yield.

EXAMPLE 6
Preparation of 2,5"-diformyl-5,2':5',2"-terselenophene.

LDA (1.0 M solution in THE, 1.0 mL) was added to an anhydrous THF solution (4 mL) containing 2,2':5',2"-terselenophene (100 mg) under N$_2$ at −78° C. The solution was stirred at −78° C. for 3 h, anhydrous DMF (2 mL) was added, stirred at −78° C. for 1 h, and slowly warmed to room temperature. The reaction solution was diluted with ethyl acetate (100 mL) and washed with H$_2$O (4×100 mL). The organic layer was separated, dried over MgSO$_4$, filtered, and the solvent was removed under vacuum. The residue was chromatographed over silica gel using (5:1) CH$_2$Cl$_2$/ethyl acetate to afford 2,5"-diformyl-5,2':5',2"-terselenophene in 75% yield.

EXAMPLE 7
Preparation of 2-hydroxymethyl-5,2':5',2"-terselenophene.

NaBH$_4$ (10 mg) was added to a THF solution (2 mL) 2-formyl-5,2':5',2"-terselenophene (15 mg) and stirred at room temperature for 2 h. The reaction solution was diluted with ethyl acetate (50 mL), washed with 2N HCl (5 mL), and then washed with H$_2$O (3×50 mL). The organic layer was separated, dried over MgSO$_4$, filtered, and the solvent was removed under vacuum. The residue was chromatographed over silica gel using (2:1) hexanes/ethyl acetate to afford 2-hydroxymethyl-5,2':5',2"-terselenophene in 98% yield.

EXAMPLE 8
Preparation of 2,5"-dihydroxymethyl-5,2':5',2"-terselenophene.

NaBH$_4$ (10 mg) was added to a THF solution (2 mL) containing 2,5"-diformyl-5,2':5',2"-terselenophene (15 mg) and stirred at room temperature for 5 h. The reaction solution was diluted with ethyl acetate (50 mL), washed with 2N HCl (5 mL), and washed with H$_2$O (3×100 mL). The organic layer was separated, dried over MgSO$_4$, filtered, and the solvent was removed under vacuum. The residue was chromatographed over silica gel using (1:1) hexanes/ethyl acetate to afford 2,5"-dihydroxymethyl-5,2':5',2"-terselenophene in 98% yield.

EXAMPLE 9
Preparation of 2,4-diselenophenylfuran.

d-10-camphorsulfonic acid (2 g) was added to an ethanolic solution (15 mL) containing 2',2"-diselenophene-1,4-diketone (100 mg) and refluxed for 2 days. The reaction solution was diluted with ethyl acetate (100 mL) and washed with H$_2$O (3×100 mL). The organic layer was separated, dried over MgSO$_4$, filtered, and the solvent was removed under vacuum. The residue was chromatographed over silica gel using (10:1) hexanes/ethyl acetate to afford 2,2':5,2"-diselenophenylfuran in 90% yield.

EXAMPLE 10
Preparation of 5'-formyl-2,2':5,2"-diselenophenylfuran.

LDA (1 molar solution in THF, 00 mL) was added to an anhydrous THF solution (00 mL) containing 2,2':5,2"-diselenophenylfuran (00 mg) under N$_2$ at −78° C. The solution was stirred at −78° C. for 3 h, anhydrous DMF (excess) was added, stirred at −78° C. for 1 h, and slowly warmed to room temperature. The reaction solution was diluted with ethyl acetate (00 mL) and washed with H$_2$O (3×100 mL). The organic layer was separated, dried over MgSO$_4$, filtered, and the solvent was removed under vacuum. The residue was chromatographed over silica gel using (4:1) hexanes/ethyl acetate to afford 5'-formyl-2,2':5,2"-diselenophenylfuran in 00% yield.

EXAMPLE 11
Preparation of 5',5"-diformyl-2,2':5,2"-diselenophenylfuran.

LDA (1 molar solution in THF, 00 mL) was added to an anhydrous THF solution (00 mL) containing 2,2':5,2"- diselenophenylfuran (00 mg) under N$_2$ at −78° C. The solution was stirred at −78° C. for 3 h, anhydrous DMF (excess) was added, stirred at −78° C. for 1 h, and slowly warmed to room temperature: The reaction solution was diluted with ethyl acetate (00 mL) and washed with H$_2$O (3×100 mL). The organic layer was separated, dried over MgSO$_4$, filtered, and the solvent was removed under vacuum. The residue was chromatographed over silica gel using (4:1) hexanes/ethyl acetate to afford 5,5"-diformyl-2,2':5,2"-diselenophenylfuran in 00% yield.

EXAMPLE 12

Preparation of 5'-hydroxymethyl-2,2':5,2"-diselenophenylfuran.

NaBH$_4$ (excess) was added to a THF solution (00 mL) containing 5'-formyl-2,2':5,2"-diselenophenylfuran (00 mg) and stirred at room temperature for 5 h. The reaction solution was diluted with ethyl acetate (100 mL) and washed with H$_2$O (3×100 mL). The organic layer was separated, dried over MgSO$_4$, filtered, and the solvent was removed under vacuum. The residue was chromatographed over silica gel using (2:1) hexanes/ethyl acetate to afford 5'-hydroxymethyl-2,2':5,2"-diselenophenylfuran in 00% yield.

EXAMPLE 13

Preparation of 5',5"-dihydroxymethyl-2,2':5,2"-diselenophenylfuran.

NaBH$_4$ (excess) was added to a THF solution (00 mL) containing 5',5"-diformyl-2,2':5,2"-diselenophenylfuran (00 mg) and stirred at room temperature for 5 h. The reaction solution was diluted with ethyl acetate (100 mL) and washed with H$_2$O (3×100 mL). The organic layer was separated, dried over MgSO$_4$, filtered, and the solvent was removed under vacuum. The residue was chromatographed over silica gel using (1:1) hexanes/ethyl acetate to afford 5',5"-dihydroxymethyl-2,2':5,2"-diselenophenylfuran in 00% yield.

EXAMPLE 14

Preparation of 2,1':5,2"-diselenophenylthiophene.

BCl$_3$ (1.0 M solution in hexanes, 580 mL) was added dropwise to an anhydrous toluene solution (5 mL) containing 2',2"-diselenophenyl-1,4-diketone (100 mg) and bis(tricyclohexyltin)sulfide (520 mg) under N$_2$ at room temperature. The solution was refluxed for 30 min and cooled to room temperature. The reaction solution was diluted with ethyl acetate (100 mL) and washed with H$_2$O (2×100 mL). The organic layer was separated, dried over MgSO$_4$, filtered, and the solvent was removed under vacuum. The residue was chromatographed over silica gel using hexanes to afford 2,2':5,2"-diselenophenylthiophene in 85% yield.

EXAMPLE 15

Preparation of 5'-formyl-2,2':5,2"-diselenophenylthiophene.

LDA (1.0 M solution in THF, 350 mL) was added to an anhydrous THF solution (4 mL) containing 2,2':5,2"-diselenophenylthiophene under N$_2$ at −78° C. The solution was stirred at −78° C. for 3 h, anhydrous DMF (1 mL) was added, stirred at −78° C. for 1 h, and slowly warmed to room temperature. The reaction solution was diluted with ethyl acetate (50 mL) and washed with H$_2$O (3×100 mL). The organic layer was separated, dried over MgSO$_4$, filtered, and the solvent was removed under vacuum. The residue was chromatographed over silica gel using CH$_2$Cl$_2$ to afford 5'-formyl-2,2':5,2"-diselenophenylthiophene in 80% yield.

EXAMPLE 16

Preparation of 5',5"-diformyl-2,2':5,2"-diselenophenylthiophene.

LDA (1.0 M solution in THF, 1 mL) was added to an anhydrous THF solution (4 mL) containing 2,2':5,2"-diselenophenylthiophene under N$_2$ at −78° C. The solution was stirred at −78° C. for 3 h, anhydrous DMF (2 mL) was added, the solution was stirred at −78° C. for 1 h, and slowly warmed to room temperature. The reaction solution was diluted with ethyl acetate (100 mL) and washed with H$_2$O (3×100 mL). The organic layer was separated, dried over MgSO$_4$, filtered, and the solvent was removed under vacuum. The residue was chromatographed over silica gel using (5:1) CH$_2$Cl$_2$/ethyl acetate to afford 5',5"-diformyl-2,2':5,2"-diselenophenylthiophene in 80% yield.

EXAMPLE 17

Preparation of 5'-hydroxymethyl-2,2':5,2"-diselenophenylthiophene.

NaBH$_4$ (10 mg) was added to a THF solution (3 mL) containing 5'-formyl-2,2':5,2"-diselenophenylthiophene (20 mg) and stirred at room temperature for 2 h. The reaction solution was diluted with ethyl acetate (50 mL) and washed with H$_2$O (5×50 mL). The organic layer was separated, dried over MgSO$_4$, filtered, and the solvent was removed under vacuum. The residue was chromatographed over silica gel using (2:1) CH$_2$Cl$_2$/ethyl acetate to afford 5'-hydroxymethyl-2,2':5,2"-diselenophenylthiophene in 98% yield.

EXAMPLE 18

Preparation of 5,5"-dihydroxymethyl-2,2':5,2"-diselenophenylthiophene.

NaBH$_4$ (10 mg) was added to a THF solution (3 mL) containing 5',5"-diformyl-2,2':5,2"-diselenophenylthiophene (20 mg) and stirred at room temperature for 5 h. The reaction solution was diluted with ethyl acetate (50 mL) and washed with H$_2$O (5×50 mL). The organic layer was separated, dried over MgSO$_4$, filtered, and the solvent was removed under vacuum. The residue was chromatographed over silica gel using (1:1) hexanes/ethyl acetate to afford 5',5"-dihydroxymethyl-2,2':5,2"-diselenophenylthiophene in 98% yield.

EXAMPLE 19

Preparation of 2,2':5,2"-diselenophenylpyrrole.

An ethanolic solution (20 mL) containing 2',2"-diselenophenyl-1,4-diketone (200 mg) and ammonium acetate (500 mg) and sodium acetate (200 mg) was refluxed overnight. The reaction solution was diluted with ethyl acetate (100 mL) and washed with H$_2$O (3×100 mL). The organic layer was separated, dried over MgSO$_4$, filtered, and the solvent was removed under vacuum. The residue was chromatographed over silica gel using (10:1) hexanes/ethyl acetate to afford 2,2':5,2"-diselenophenylpyrrole in 94% yield.

EXAMPLE 20

Preparation of 5'-formyl-2,2':5,2"-diselenophenylpyrrole.

LDA (1.0 M solution in THF, 760 mL) was added to an anhydrous THF solution (5 mL) containing 2,2':5,2"-diselenophenylpyrrole (100 mg) under N$_2$ at −78° C. The solution was stirred at −78° C. for 3 h, anhydrous DMF (1.5 mL) was added, the solution was slowly warmed to room temperature, and stirred at room temperature for 2 h. The reaction solution was diluted with ethyl acetate (100 mL) and washed with H$_2$O (3×100 mL). The organic layer was separated, dried over MgSO$_4$, filtered, and the solvent was removed under vacuum. The residue was chromatographed over silica gel using (3:1) hexanes/ethyl acetate to afford 5'-formyl-2,2':5,2"-diselenophenylpyrrole in 75% yield.

EXAMPLE 21
Preparation of 5'-hydroxymethyl-2,2':5,2"-diselenophenylpyrrole.

$NaBH_4$ (20 mg) was added to a THE solution (2 mL) containing 5'-formyl-2,2':5,2"-diselenophenylpyrrole (20 mg) and stirred at room temperature for 2 h. The reaction solution was diluted with ethyl acetate (50 mL) and washed with $H_2O$ (3×50 mL). The organic layer was separated, dried over $MgSO_4$, filtered, and the solvent was removed under vacuum. The residue was chromatographed over silica gel using (2:1) hexanes/ethyl acetate to afford 5'-hydroxymethyl-2,2':5,2"-diselenophenylpyrrole in 98% yield.

EXAMPLE 22
Preparation of 2',2"-difuranyl-1,4-diketone.

A $CH_2Cl_2$ solution containing furan (10 mL) and succinyl chloride (2 g) was added dropwise to an anhydrous $CH_2Cl_2$ solution (100 mL) containing $AlCl_3$ (10 g) under $N_2$ at 0° C. The reaction mixture was stirred at 0° C. for 2 h, slowly warmed to room temperature, and stirred for 4 h. The reaction mixture was poured into a beaker containing ice. Ethyl acetate (300 mL) was added and the organic layer was separated out using a separatory funnel. The aqueous layer was back washed with ethyl acetate (2×100 mL). The combined organic layer was washed with $H_2O$ (2×300 mL). The organic layer was collected, dried over $MgSO_4$, and the solvent was removed under vacuum. The residue was chromatographed over silica gel using (3:1) hexanes/ethyl acetate to afford 2',2"-difuranyl-1,4-diketone in 25% yield.

EXAMPLE 23
Preparation of 2,2':5,2"-difuranylselenophene.

$BCl_3$ (1.0 M solution in hexanes, 900 ml) was added dropwise to an anhydrous, toluene solution (00 mL) containing 2',2"-difuranyl-1,4-diketone (100 mg) and bis(tricyclohexyltin)-selenide (750 mg) under $N_2$ at room temperature. The solution was refluxed for 30 min and cooled to room temperature. The reaction solution was diluted with ethyl acetate (100 mL) and washed with $H_2O$ (2×100 mL). The organic layer was separated, dried over $MgSO_4$, filtered, and the solvent was removed under vacuum. The residue was chromatographed over silica gel using hexanes to afford 2,2':5,2"-difuranylselenophene in 80% yield.

EXAMPLE 24
Preparation of 5'-formyl-2,2':5,2"-difuranylselenophene.

LDA (1.0 M solution in THF, 420 mL) was added to an anhydrous THF solution (4 mL) containing 2,2':5,2"-difuranylselenophene (100 mg) under $N_2$ at −78° C. The solution was stirred at −78° C. for 3 h, anhydrous DMF (1 mL) was added, the solution was stirred at −78° C. for 1 h, and slowly warmed to room temperature. The reaction solution was diluted with ethyl acetate (100 mL) and washed with $H_2O$ (3×100 mL). The organic layer was separated, dried over $MgSO_4$, filtered, and the solvent was removed under vacuum. The residue was chromatographed over silica gel using (3:1) hexanes/ethyl acetate to afford 5'-formyl-2,2':5,2"-difuranylselenophene in 75% yield.

EXAMPLE 25
Preparation of 5',5"-diformyl-2,2':5,2"-difuranylselenophene.

LDA (1.0 M solution in THF, 00 mL) was added to an anhydrous THF solution (4 mL) containing 2,2':5,2"-difuranylselenophene (100 mg) under $N_2$ at −78° C. The solution was stirred at −78° C. for 3 h, added anhydrous DMF (2 mL), stirred at −78° C. for 1 h, and slowly warmed to room temperature. The reaction solution was diluted with ethyl acetate (100 mid) and washed with $H_2O$ (3×100 nm). The organic layer was separated, dried over $MgSO_4$, filtered, and the solvent was removed under vacuum. The residue was chromatographed over silica gel using (2:1) hexanes/ethyl acetate to afford 5',5"-diformyl-2,2':5,2"-difuranylselenophene in 80% yield.

EXAMPLE 26
Preparation of 5'-hydroxymethyl-2,2':5,2"-difuranylselenophene.

$NaBH_4$ (10 mg) was added to a THF solution (2 mL) containing 5'-formyl-2,2':5,2"-difuranylselenophene (20 mg) and stirred at room temperature for 5 h. The reaction solution was diluted with ethyl acetate (50 mL) and washed with $H_2O$ (3×50 mL). The organic layer was separated, dried over $MgSO_4$, filtered, and the solvent was removed under vacuum. The residue was chromatographed over silica gel using (2:1) hexanes/ethyl acetate to afford 5'-hydroxymethyl-2,2':5,2"-difuranylselenophene in 98% yield.

EXAMPLE 27
Preparation of 5',5"-dihydroxymethyl-2,2':5,2"-difuranylselenophene.

$NaBH_4$ (10 mg) was added to a THF solution (2 mL) containing 5',5"-diformyl-2,2':5,2"-difuranylselenophene (20 mg) and stirred at room temperature for 5 h. The reaction solution was diluted with ethyl acetate (50 mL) and washed with $H_2O$ (3×50 mL). The organic layer was separated, dried over $MgSO_4$, filtered, and the solvent was removed under vacuum. The residue was chromatographed over silica gel using (1:1) hexanes/ethyl acetate to afford 5',5"-dihydroxymethyl-2,2':5,2"-difuranylselenophene in 98% yield.

EXAMPLE 28
Preparation of 2',2"-dithienyl-1,4-diketone.

A $CH_2Cl_2$ solution-containing thiophene (10 mL) and succinyl chloride (2 g) was added dropwisely to an anhydrous $CH_2Cl_2$ solution (100 mL) containing $AlCl_3$ (10 g) under $N_2$ at 0° C. The reaction mixture was stirred at 0° C. for 2 h, slowly warmed to room temperature, and stirred for 4 h. The reaction mixture was poured into a beaker containing ice. Ethyl acetate (300 mL) was added and the organic layer was separated out using a separatory funnel. The aqueous layer was back washed with ethyl acetate (2×100 mL). The combined organic layer was washed with $H_2O$ (2×300 mL). The organic layer was collected, dried over $MgSO_4$, and the solvent was removed under vacuum. The residue was chromatographed over silica gel using (3:1) hexanes/ethyl acetate to afford 2',2"-dithienyl-1,4-diketone in 25% yield.

EXAMPLE 29
Preparation of 2,2':5,2"-dithienylselenophene.

$BCl_3$ (1.0 M solution in hexanes, 1.6 mL) was added dropwise to an anhydrous toluene solution (5 mL) containing 2',2"-dithienyl-1,4-diketone (200 mg) and bis(tricyclohexyltin)selenide (1.3 g) under $N_2$ at room temperature. The solution was refluxed for 30 min and cooled to room temperature. The reaction solution was diluted with ethyl acetate (100 mL) and washed with $H_2O$ (3×100 mL). The organic layer was separated, dried over $MgSO_4$, filtered, and the solvent was removed under vacuum. The residue was chromatographed over silica gel using hexanes to afford. 2,2':5,2"-dithienylselenophene in 90% yield.

EXAMPLE 30
Preparation of 5'-formyl-2,2':5,2"-dithienylselenophene.

LDA (1.0 M solution in THF, 380 mL) was added to an anhydrous THF solution (4 mL) containing 2,2':5,2"-dithienylselenophene (100 mg) under $N_2$ at −78° C. The solution was stirred at −78° C. for 3 h, anhydrous DMF (1 mL) was added, the solution stirred at −78° C. for 1 h, and slowly warmed to room temperature. The reaction solution was diluted with ethyl acetate (100 mL) and washed with $H_2O$ (3×100 mL). The organic layer was separated, dried over $MgSO_4$, filtered, and the solvent was removed under vacuum. The residue was chromatographed over silica gel using (3:1) hexanes/ethyl acetate to afford 5'-formyl-2,2':5,2"-dithienylselenophene in 75% yield.

EXAMPLE 31
Preparation of 5',5"-diformyl-2,2':5,2"-dithienylselenophene.

LDA (1.0 M solution in THF, 1.0 mL) was added to an anhydrous THF solution (4 mL) containing 2,2':5,2"-dithienylselenophene (100 mg) under $N_2$ at −78° C. The solution was stirred at −78° C. for 3 h, anhydrous DMF (2 mL) was added, the solution stirred at −78° C. for 1 h, and slowly warmed to room temperature. The reaction solution was diluted with ethyl acetate (100 mL) and washed with $H_2O$ (3×100 mL). The organic layer was separated, dried over $MgSO_4$, filtered, and the solvent was removed under vacuum. The residue was chromatographed over silica gel using (2:1) hexanes/ethyl acetate to afford 5',5"-diformyl-2,2':5,2"-dithienylselenophene in 85% yield.

EXAMPLE 32
Preparation of 5'-hydroxymethyl-2,2':5,2"-dithienylselenophene.

$NaBH_4$ (10 mg) was added to a THF solution (2 mL) containing 5'-formyl-2,2':5,2"-dithienylselenophene (20 mg) and stirred at room temperature for 5 h. The reaction solution was diluted with ethyl acetate (50 mL) and washed with $H_2O$ (3×50 mL). The organic layer was separated, dried over $MgSO_4$, filtered, and the solvent was removed under vacuum. The residue was chromatographed over silica gel using (2:1) hexanes/ethyl acetate to afford 5'-hydroxymethyl-2,2':5,2"-dithienylselenophene in 98% yield.

EXAMPLE 33
Preparation of 5',5"-dihydroxymethyl-2,2':5,2"-dithienylselenophene.

$NaBH_4$ (10 mg) was added to a THF solution (2 mL) containing 5',5"-diformyl-2,2':5,2"-dithienylselenophene (20 mg) and stirred at room temperature for 5 h.

What is claimed is:

1. A compound having the formula:

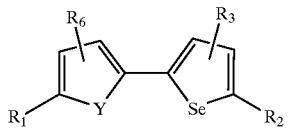

wherein $R_1, R_2, R_3$, and $R_6$ are each independently selected from the group consisting of hydrogen, $CH_2OH$, CHO, and $CH_2NH_2$;

Y is selected from the group consisting of selenium, sulfur, oxygen, and NR, wherein R is hydrogen or $C_1$–$C_7$ alkyl;

and when at least one of $R_1$, $R_2$, $R_3$, or $R_6$ is $CH_2NH_2$, a pharmaceutically acceptable salt of the compound represented thereby; with the proviso that when $R_1$ and $R_2$ are both hydrogen, $R_3$ and $R_6$ are not both hydrogen.

2. The compound of claim 1, wherein $R_3$ and $R_6$ are hydrogen.

3. The compound of claim 1, wherein the compound is complexed with a cyclodextrin.

4. A compound having the formula:

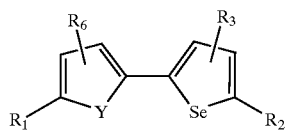

wherein $R_1$, $R_2$, $R_3$, and $R_6$ are each independently selected from the group consisting of hydrogen, CHO, $CH_2OH$, and $CH_2NH_2$;

Y is selected from the group consisting of selenium, sulfur, oxygen, and NR, wherein R is hydrogen or $C_1$–$C_7$ alkyl;

and when at least one of $R_1$, $R_2$, $R_3$, or $R_6$ is $CH_2NH_2$, a pharmaceutically acceptable salt of the compound represented thereby; with the proviso that $R_1$ and $R_2$ are not both hydrogen.

5. The compound of claim 4, wherein the compound is complexed with a cyclodextrin.

6. A pharmaceutical composition comprising a compound having the formula:

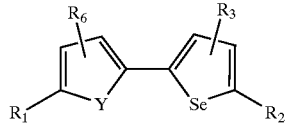

wherein $R_1$, $R_2$ $R_3$, and $R_6$ are each independently selected from the group consisting of hydrogen, $CH_2OH$, CHO, and $CH_2NH_2$;

Y is selected from the group consisting of selenium, sulfur, oxygen, and NR, wherein R is hydrogen or $C_1$–$C_7$ alkyl;

and when at least one of $R_1$, $R_2$, $R_3$, or $R_6$ is $CH_2NH_2$, a pharmaceutically acceptable salt of the compound represented thereby; with the proviso that at least one of $R_1$, $R_2$, $R_3$, or $R_6$ is other than hydrogen;

and a pharmaceutically acceptable carrier.

7. The composition of claim 6, wherein $R_3$ and $R_6$ in the compound are hydrogen.

8. The pharmaceutical composition of claim 6, wherein the compound is complexed with a cyclodextrin.

\* \* \* \* \*

UNITED STATES PATENT AND TRADEMARK OFFICE
CERTIFICATE OF CORRECTION

PATENT NO. : 6,894,039 B2  
DATED : May 17, 2005  
INVENTOR(S) : Ching-jer Chang et al.

It is certified that error appears in the above-identified patent and that said Letters Patent is hereby corrected as shown below:

Title page,
Item [62], Related U.S. Application Data, delete the following:
"filed as application No. PCT/US97/09717 on Nov. 11, 1998, now abandoned."
after "Application No. 09/180,154", add -- filed on November 11, 1998, now abandoned, which is a U.S. national application of international application Serial No. PCT/US97/09717, filed on June 3, 1997. --

Signed and Sealed this

Nineteenth Day of July, 2005

JON W. DUDAS
*Director of the United States Patent and Trademark Office*